United States Patent
Stewart (10) Patent No.: US 10,147,221 B2
(45) Date of Patent: Dec. 4, 2018

(54) VISUAL FUNCTION TARGETING USING RANDOMIZED, DYNAMIC, CONTRASTING FEATURES

(71) Applicant: Konan Medical USA, Inc., Irvine, CA (US)

(72) Inventor: Charles W. Stewart, Laguna Beach, CA (US)

(73) Assignee: Konan Medical USA, Inc., Irvine, CA (US)

(*) Notice: Subject to any disclaimer, the term of this patent is extended or adjusted under 35 U.S.C. 154(b) by 0 days.

(21) Appl. No.: 15/457,184

(22) Filed: Mar. 13, 2017

(65) Prior Publication Data

US 2017/0186210 A1    Jun. 29, 2017

Related U.S. Application Data

(63) Continuation of application No. 14/571,174, filed on Dec. 15, 2014, now Pat. No. 9,595,126.

(51) Int. Cl.
*G06T 15/00* (2011.01)
*G06T 13/80* (2011.01)
(Continued)

(52) U.S. Cl.
CPC .......... *G06T 13/80* (2013.01); *A61B 3/0041* (2013.01); *G06T 11/001* (2013.01); *G06T 3/40* (2013.01);
(Continued)

(58) Field of Classification Search
CPC ......... G06T 13/80; G06T 11/001; G06T 3/40; G06T 2210/41; G06T 2210/62; A61B 3/0041
(Continued)

(56) References Cited

U.S. PATENT DOCUMENTS 3,807,839 A    4/1974  Sugarman et al.
4,257,690 A    3/1981  Howland
(Continued)

FOREIGN PATENT DOCUMENTS

DE    19543050 A1    2/1997
DE    19948722 A1    5/2001
(Continued)

OTHER PUBLICATIONS

Gantz, Liat, and Harold E. Bedell. "Variation of stereothreshold with random-dot stereogram density." Optometry and vision science: official publication of the American Academy of Optometry 88.9 (2011): 1066.*

(Continued)

*Primary Examiner* — Phu K Nguyen
(74) *Attorney, Agent, or Firm* — LaBatt, LLC (57) ABSTRACT

A solution for targeting a visual function of an observer is provided. The solution presents an animation for display to an observer. The animation includes a background and at least a portion of the animation also includes one or more foreground areas, each of which is located in a portion of the background. The background and the foreground area(s) include a set of common attributes substantially continuously changing during the animation and at least one different attribute between the background and the foreground area. At least one attribute of the background changes randomly during the animation. The at least one different attribute targets the visual function.

25 Claims, 3 Drawing Sheets

(51) Int. Cl.
   *G06T 11/00* (2006.01)
   *A61B 3/00* (2006.01)
   *G06T 3/40* (2006.01)

(52) U.S. Cl.
   CPC ...... *G06T 2210/41* (2013.01); *G06T 2210/62* (2013.01)

(58) Field of Classification Search
   USPC .................................................. 345/419, 418
   See application file for complete search history.

(56) References Cited

U.S. PATENT DOCUMENTS

| | | | |
|---|---|---|---|
| 4,529,280 A | 7/1985 | Nohda | |
| 4,541,697 A | 9/1985 | Remijan | |
| 4,607,923 A | 8/1986 | Task et al. | |
| 4,611,893 A | 9/1986 | Schrier | |
| 4,615,594 A | 10/1986 | Task | |
| 4,861,156 A | 8/1989 | Terry | |
| 5,914,772 A | 6/1999 | Dyer | |
| 5,953,102 A | 9/1999 | Berry | |
| 6,402,320 B1 | 6/2002 | Borchert | |
| 6,592,223 B1 | 7/2003 | Stern et al. | |
| 7,267,439 B2 | 9/2007 | Toshima et al. | |
| 7,334,895 B2 | 2/2008 | Kandel et al. | |
| 7,350,921 B2 | 4/2008 | Ridings | |
| 7,367,675 B2 | 5/2008 | Maddalena et al. | |
| 7,396,128 B2 | 7/2008 | Feher et al. | |
| 7,429,109 B2 | 9/2008 | Toshima et al. | |
| 8,083,353 B2 | 12/2011 | Hytowitz | |
| 8,144,399 B2 | 3/2012 | Steenblik et al. | |
| 8,337,019 B2 | 12/2012 | Murray et al. | |
| 8,702,238 B2 * | 4/2014 | Berry ................. | A61B 3/18 351/223 |
| 9,089,257 B2 | 7/2015 | Hofeldt | |
| 9,314,154 B2 * | 4/2016 | Palanker ............. | A61B 3/0025 |
| 9,572,484 B2 * | 2/2017 | Palanker ............. | G06Q 50/22 |
| 9,595,126 B2 | 3/2017 | Stewart | |
| 2004/0046934 A1 | 3/2004 | Sponsel et al. | |
| 2005/0225720 A1 | 10/2005 | Ridings | |
| 2006/0203195 A1 | 9/2006 | Squire et al. | |
| 2007/0121066 A1 | 5/2007 | Nashner | |
| 2008/0186450 A1 | 8/2008 | Holladay | |
| 2008/0309880 A1 | 12/2008 | Fisher et al. | |
| 2011/0001924 A1 | 1/2011 | Giraudet et al. | |
| 2011/0037950 A1 | 2/2011 | Hytowitz | |
| 2011/0228227 A1 | 9/2011 | Roser | |
| 2011/0255055 A1 | 10/2011 | Spaeth et al. | |
| 2012/0327369 A1 | 12/2012 | Hytowitz | |
| 2013/0141697 A1 | 6/2013 | Berry et al. | |
| 2013/0194317 A1 | 8/2013 | Guillon et al. | |
| 2014/0293228 A1 | 10/2014 | Hytowitz | |
| 2016/0035122 A1 | 2/2016 | Stewart et al. | |

FOREIGN PATENT DOCUMENTS

| | | |
|---|---|---|
| EP | 1336924 A1 | 8/2003 |
| EP | 2014222 A1 | 1/2009 |
| JP | 2007061416 A | 3/2007 |

OTHER PUBLICATIONS

Toufeeq, A. "Specifying colours for colour vision testing using computer graphics." Eye 18.10 (2004): 1001-1005.*
Greenwood, et al., "Visual Acuity, Crowding, and Stereo-Vision Are Linked in Children with and without Amblyopia," Visual Psychophysics and Physiological Optics, Nov. 2012, 29 pages, vol. 53, No. 12.
Marko, et al., "Contrast independence of dynamic random dot correlogram evoked VEP amplitude," Journal of Vision, 2009, 18 pages, vol. 9, No. 8.
Sharpe, C.R., "The Visibility and Fading of Thin Lines Visualized by their Controlled Movement Across the Retina," J Physiol., Apr. 1972, 22 pages.
"Troxler's Fading," Accessed Jul. 30, 2017, 3 pages, http://en.wikipedia.org/wiki/Troxler%27s_fading.
Watt, W., "Computer Vision Syndrome and Computer Glasses," Oct. 25, 2003, 7 pages, http://www.mdsupport.org/library/cvs.html.
Craddock, R., U.S. Appl. No. 14/447,794, Final Rejection1, dated May 8, 2017, 19 pages.
Craddock, R., U.S. Appl. No. 14/447,794, Non-Final Rejection1, dated Aug. 24, 2016, 18 pages.
Wilkes, U.S. Appl. No. 12/583,255, Notice of Allowance, dated Aug. 24, 2011, 7 pages.
Stultz, J., U.S. Appl. No. 12/583,225, Final Office Action, dated Mar. 8, 2011, 8 pages.
Stultz, J., U.S. Appl. No. 12/583,225, Non-Final Office Action, dated Sep. 27, 2010, 5 pages.
Dinh, J., U.S. Appl. No. 13/337,277, Notice of Allowance, dated Apr. 3, 2014, 11 pages.
Dinh, J., U.S. Appl. No. 13/337,277, Non-Final Office Action, dated Sep. 4, 2013, 4 pages.
Dinh, J., U.S. Appl. No. 14/303,001, Non-Final Office Action, dated Oct. 30, 2015, 4 pages.
Nguyen, P. U.S. Appl. No. 14/571,174, Notice of Allowance, dated Nov. 4, 2016, 12 pages.
Nguyen, P. U.S. Appl. No. 14/571,174, Non-Final Office Action, dated Apr. 22, 2016, 43 pages.
Kim, International Search Report for International Application No. PCT/US2015/042065, dated Oct. 29, 2015, 13 pages.
Kim, International Search Report for International Application No. PCT/US2015/065657, dated Mar. 31, 2016, 5 pages.
Kim, International Search Report for International Application No. PCT/US2010045798, dated Apr. 28, 2011, 3 pages.
Gartner, European Search Report and Written Opinion for European Patent Application No. EP10810509, dated Jan. 17, 2013, 12 pages.

* cited by examiner

VISUAL FUNCTION TARGETING USING RANDOMIZED, DYNAMIC, CONTRASTING FEATURES

REFERENCE TO RELATED APPLICATION

The current application is a continuation of U.S. application Ser. No. 14/571,174, filed on 15 Dec. 2014, which is hereby incorporated by reference.

TECHNICAL FIELD

The disclosure relates generally to visual assessment, and more particularly, to assessing one or more visual functions using a background and foreground, at least one of which includes randomized, dynamic, contrasting features.

BACKGROUND ART

Visual acuity, or clearness of vision, is defined as an ability to perceive or resolve a linear minimum angle of separation or "Minimum Angle of Resolution" between two stationary lines or points. Visual Acuity and other important attributes of vision, such as contrast sensitivity, color vision deficiencies, and depth perception have historically been measured using content, such as letters, shapes, or pictograms identified by a subject that also necessitate language specific literacy or ability to cognitively associate or name objects. Such letters, shapes, or pictograms may have poor cross-cultural familiarity, such as with Asian or Arabic cultures identifying Roman letters, or may require a mental age threshold to understand letters or pictograms presented and then cognitively process into verbal or other responses, thereby additionally testing a cognitive process rather than the strictly the targeted visual function.

SUMMARY OF THE INVENTION

Aspects of the invention provide a solution for targeting one or more visual functions using an animation including a background with and a foreground, at least one of which includes randomized, dynamic, contrasting features. For example, in an embodiment of the solution, the animation includes a background and at least a portion of the animation also includes one or more foreground areas, each of which is located in a portion of the background. The background and the foreground area(s) include a set of common attributes substantially continuously changing during the animation and at least one different attribute between the background and the foreground area. At least one attribute of the background changes randomly during the animation. The at least one different attribute targets the visual function. The solution can be implemented as part of a solution for assessing the visual function(s).

A first aspect of the invention provides a computer-implemented method of targeting a visual function of an observer, the method including: generating an animation including a background, wherein at least a portion of the animation further includes a foreground area in a portion of the background, wherein the background and the foreground area include a set of common attributes substantially continuously changing during the animation and at least one different attribute between the background and the foreground area, wherein the at least one different attribute targets the visual function, and wherein at least one attribute of the background changes randomly during the animation; and providing the animation for display to the observer.

A second aspect of the invention provides a computer-implemented method of assessing a visual function of an observer, the method including: generating, using a computer system, an animation including a background, wherein at least a portion of the animation further includes a foreground area in a portion of the background, wherein the background and the foreground area include a set of common attributes substantially continuously changing during the animation and at least one different attribute between the background and the foreground area, wherein the at least one different attribute targets the visual function, and wherein at least one attribute of the background changes randomly during the animation; providing the animation for display to the observer on a display device; receiving, at the computer system, an indication corresponding to an ability of the observer to perceive the foreground area; and providing the indication for use in assessing the target visual function of the observer.

A third aspect of the invention provides a computer-implemented method of assessing a visual function of an observer, the method including: presenting, using a computer system, an animation including a background for to the observer on a display device, wherein at least a portion of the animation further includes a foreground area in a portion of the background, wherein the background and the foreground area include a set of common attributes substantially continuously changing during the animation and at least one different attribute between the background and the foreground area, wherein the at least one different attribute targets the visual function, and wherein at least one attribute of the background changes randomly during the animation; receiving, at the computer system, an indication corresponding to an ability of the observer to perceive the foreground area; and providing the indication for use in assessing the target visual function of the observer.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for targeting one or more visual functions using a background and a foreground, at least one of which includes randomized, dynamic, contrasting features. The foreground can include one or more foreground areas ("blobs"), each of which can have regular or irregular dimensions, with similar randomized and dynamic features as the background, but with a partially or fully different set of contrasting features. These foreground blob(s) can occupy different locations in the background and can move during their presentation to a user. For example, in an embodiment of the solution, the animation includes a background and at least a portion of the animation also includes one or more foreground areas, each of which is located in a portion of the background. The background and the foreground area(s) include a set of common attributes substantially continuously changing during the animation and at least one different attribute between the background and the foreground area. At least one attribute of the background changes randomly during the animation. The at least one different attribute targets the visual function. The solution can be implemented as part of a solution for assessing the visual function(s).

As used herein, unless otherwise noted, the term "set" means one or more (i.e., at least one) and the phrase "any solution" means any now known or later developed solution. Similarly, as used herein, unless otherwise noted, the term "random" and its related forms are inclusive of any non-distinct and/or non-recurring pattern. To this extent, random includes pseudorandom patterns, patterns generated in a predetermined manner, and/or the like, which mimic a random pattern to a sufficient degree that a typical human will be unable to detect the pattern and/or have great difficulty in detecting the pattern. As used herein, unless otherwise noted, the term "approximate" and its related forms means the same or nearly the same (e.g., within ten percent of one another, or five percent in a more particular embodiment).

Figure 1:
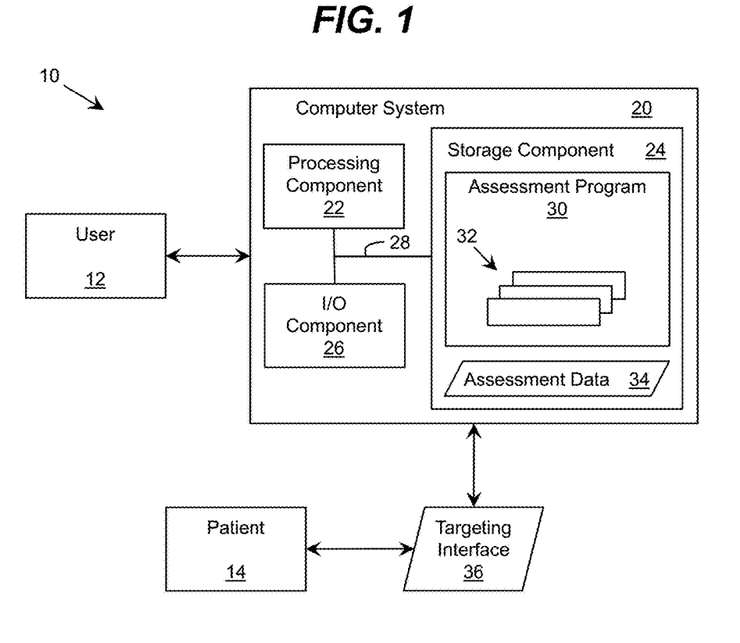
FIG. 1 shows an illustrative environment for assessing a performance level of a patient with respect to one or more visual functions according to an embodiment.

Turning to the drawings, FIG. 1 shows an illustrative environment 10 for assessing a performance level of a patient 14 with respect to one or more visual functions according to an embodiment. To this extent, the environment 10 includes a computer system 20 that can perform a process described herein in order to assess the performance level of the patient 14 with respect to a visual function. In particular, the computer system 20 is shown including an assessment program 30, which makes the computer system 20 operable to assess the performance level of the patient 14 with respect to the visual function(s) by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the assessment program 30, which is at least partially fixed in storage component 24. While executing program code, the processing component 22 can process data, which can result in reading and/or writing transformed data from/to the storage component 24 and/or the I/O component 26 for further processing. The pathway 28 provides a communications link between each of the components in the computer system 20. The I/O component 26 can comprise one or more human I/O devices, which enable a human user 12 to interact with the computer system 20 and/or one or more communications devices to enable a system user 12 to communicate with the computer system 20 using any type of communications link. To this extent, the assessment program 30 can manage a set of interfaces (e.g., graphical user interface(s), application program interface, and/or the like) that enable human and/or system users 12 to interact with the assessment program 30. Furthermore, the assessment program 30 can manage (e.g., store, retrieve, create, manipulate, organize, present, etc.) the data, such as assessment data 34, using any solution.

In any event, the computer system 20 can comprise one or more general purpose computing articles of manufacture (e.g., computing devices) capable of executing program code, such as the assessment program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the assessment program 30 can be embodied as any combination of system software and/or application software.

Furthermore, the assessment program 30 can be implemented using a set of modules 32. In this case, a module 32 can enable the computer system 20 to perform a set of tasks used by the assessment program 30, and can be separately developed and/or implemented apart from other portions of the assessment program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the assessment program 30 fixed thereon (e.g., one or more modules 32). However, it is understood that the computer system 20 and the assessment program 30 are only representative of various possible equivalent computer systems that may perform a process described herein. To this extent, in other embodiments, the functionality provided by the computer system 20 and the assessment program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

To this extent, the user 12 and/or the patient 14 can be a computer system, either of which also can be a general purpose computer system as described herein in conjunction with the computer system 20. When the user 12 and/or the patient 14 is a computer system, the computer system 20 can generate a user interface, such as a graphical user interface, for presentation to an individual utilizing the user 12 and/or the patient 14. Alternatively, the user 12 and/or the patient 14 can be an individual. In this case, the computer system 20 can generate and present the user interface to the user 12 and/or the patient 14. In either case, the user 12 and patient 14 can be different computer systems/individuals or the same computer system/individual. More particular illustrative environments 10 include: a visual assessment system (e.g., including a programmed computing device and an interface for providing a controlled viewing environment); a desktop/laptop computing device executing program code installed thereon; a tablet computing device executing an app installed thereon, which can interact with a programmed server over a network; a computing device using a browser to communicate to a programmed server over a network, such as the Internet, and/or the like.

As described herein, the computer system 20 can assess a performance level of a patient 14 with respect to one or more visual functions. It is understood that the patient 14 can be a human or other animal for which one or more visual functions are to be assessed. The assessment can be performed in a medical environment, such as a physician's office, an optometrist's office, and/or the like, or in any environment selected by the patient 14, such as his/her home, office, and/or the like. In an embodiment, some or all of the assessment is performed by a professional, such as a user 12 who is a medical practitioner (general practice or specialist), an optometrist, and/or the like. In an alternative embodiment, the assessment is self-administered by the patient 14. Regardless, when the user 12, such as a professional, is different from the patient 14, it is understood that the user 12 and patient 14 can be at the same location or remotely located from one another.

Figure 2A:
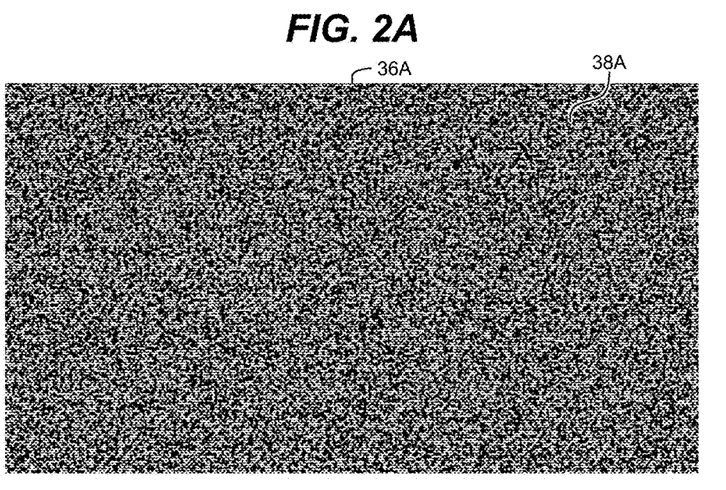
FIGS. 2A and 2B show illustrative targeting interfaces according to embodiments.
Figure 2B:
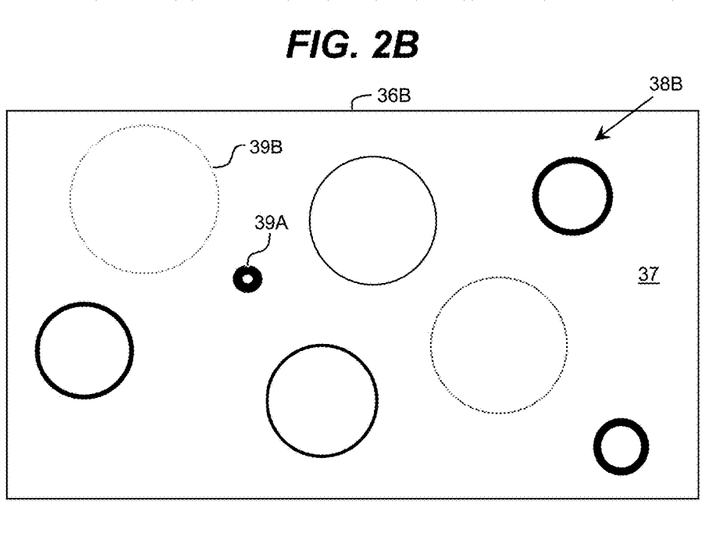

FIGS. 2A and 2B show illustrative targeting interfaces 36A, 36B, respectively, according to embodiments. Referring to FIGS. 1-2B, each targeting interface 36A, 36B is shown having a background 38A, 38B, respectively, including randomized, dynamic, contrasting features (e.g., noise). In the targeting interface 36A, the background 38A includes a random arrangement of pixels of two or more colors (e.g., random noise). In this case, the entire background 38A can include a random arrangement of pixels of two or more colors (e.g., white noise), which substantially continuously changes in an animation presented for display to the patient 14. For example, when presented for display to a patient 14, the targeting interface 36A can comprise an animation including a background 38A having an appearance similar to that of noise displayed by an analog television when no transmission signal is received.

In an embodiment of the targeting interface 36A, the background 38A does not include any pre-determined geometric shapes formed by the pixels of differing colors. The background 38A can have any relative distribution of pixels assigned to each of the plurality of colors. In an embodiment, the background 38A can comprise an approximately equal amount of each of the colors. Additionally, the pixels of each color can have an approximately uniform distribution across the entire area of the targeting interface 36A. Alternatively, the pixels of a color can be unevenly distributed, e.g., to target a particular area in the field of view of the patient 14. Regardless, the computer system 20 can generate an animation including the background 38A such that the distribution of pixels is substantially continually changing using any solution. In an illustrative embodiment, the targeting interface 36A, 36B can include any number of defined colors in a range of two to ten colors.

In the targeting interface 36B, the animation includes a background 38B having noise comprising a background area 37 of a first color with a set of randomly located substantially continuously changing background FIGS. 39A, 39B, each of which is a different color from the color of the background area 37. In an embodiment, after appearing at a location, a size of an area occupied by the background FIG. 39A, 39B substantially continuously increases, a brightness of the background FIG. 39A, 39B substantially continuously decreases, a contrast of the background FIG. 39A, 39B substantially continuously decreases, and/or the like, during the animation before the background FIG. 39A, 39B disappears from the background 38B. For example, the background FIG. 39A can correspond to a figure having just appeared in the background 38B, while the background FIG. 39B can correspond to a figure about to disappear from the background 38B. Furthermore, a central portion of the background FIG. 39A, 39B can have the same color as the background area 37 (e.g., be transparent) and the background FIG. 39A, 39B can remain centered at a fixed location within the targeting interface 36B for the entire duration that the background FIG. 39A, 39B is present within the background 38B of the animation. In an embodiment, a background FIG. 39A, 39B is generally elliptical (e.g., a circle in a more specific embodiment) with a central region that is the same color as the background area 37. In this case, the background FIG. 39A, 39B can have an appearance that mimics a surface of a standing pool of water after a rain drop has contacted the surface. Furthermore, the background 38B of the animation can include multiple background FIGS. 39A, 39B, each appearing at a different location and different time, e.g., thereby mimicking a light rain shower when the background FIGS. 39A, 39B are expanding ellipses. To this extent, as illustrated in the targeting interface 36B, the background 38B can concurrently include multiple background FIGS. 39A, 39B having appeared at different times, having varying sizes, and being located in varying locations distributed in a roughly equal amount across the entire area of the targeting interface 36B. Furthermore, the background FIGS. 39A, 39B can remain visible for varying amounts of time, can have attributes that change at varying rates, and/or the like.

It is understood that elliptical background FIGS. 39A, 39B that remain centered at a fixed location within the background 38B while getting substantially continuously larger, fainter, and/or the like, are only illustrative of various types of background figures that can be utilized in embodiments described herein. To this extent, embodiments can include any combination of one or more background figures, each of which can have a defined or amorphous boundary (e.g., a regular or irregular shape) and can have one or more attributes that substantially continuously change during the animation in any manner. For example, a background figure may get larger or smaller, may get lighter or darker, may appear and disappear, can change color(s), can have a size and/or brightness that pulses, can change location within the background 38B (e.g., be moving), and/or the like. Furthermore, the background FIGS. 39A, 39B can be a solid color (e.g., filled central region). The background FIGS. 39A, 39B can remain in the background 38B for any duration. In an illustrative embodiment, the background FIGS. 39A, 39B remain present in the background 38B for a period in a range of approximately 0.1 seconds to approximately ten seconds. In a more particular illustrative embodiment, the background FIGS. 39A, 39B can have fade in and fade out times, each of which is in a range of zero to approximately three seconds and a display interval of approximately 0.1 seconds to approximately ten seconds.

The targeting interfaces 36A, 36B can be used to target one or more visual functions, e.g., as part of a solution for assessing the corresponding visual function. In an embodiment, at least some portions of the animation can include one or more secondary noise areas (foreground areas or blobs) superimposed on the corresponding background 38A, 38B. The computer system 20 can locate the foreground blob(s) in random location(s) of the background 38A, 38B (e.g., using a randomizing solution). Alternatively, the computer system 20 can locate the foreground blob(s) in one or more predetermined locations of the background 38A, 38B, e.g., to target a particular area of the visual field of the patient 14. In the latter case, the computer system 20 can use a randomizing solution to select the order in which the foreground blob(s) are located in each of a plurality of predetermined locations (e.g., selecting a random location at which to dynamically superimpose the foreground blob(s), selecting a random one of a plurality of stored videos, and/or the like).

Figure 3A:
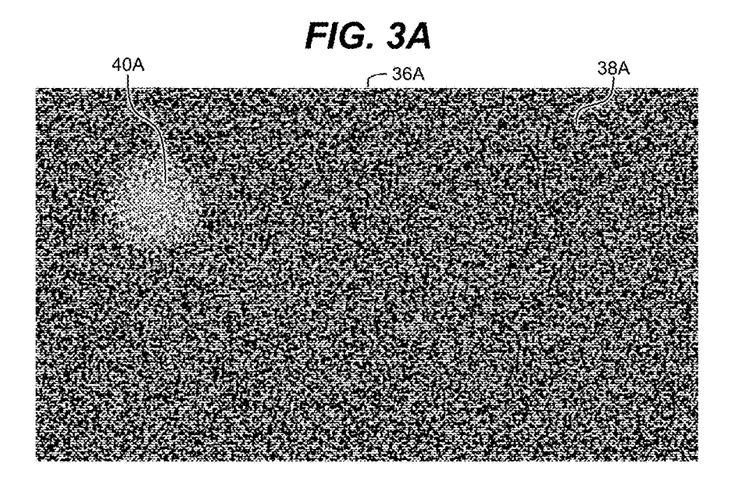
FIGS. 3A and 3B show the targeting interfaces of FIGS. 2A and 2B including illustrative foreground areas ("blobs") according to an embodiment.
Figure 3B:
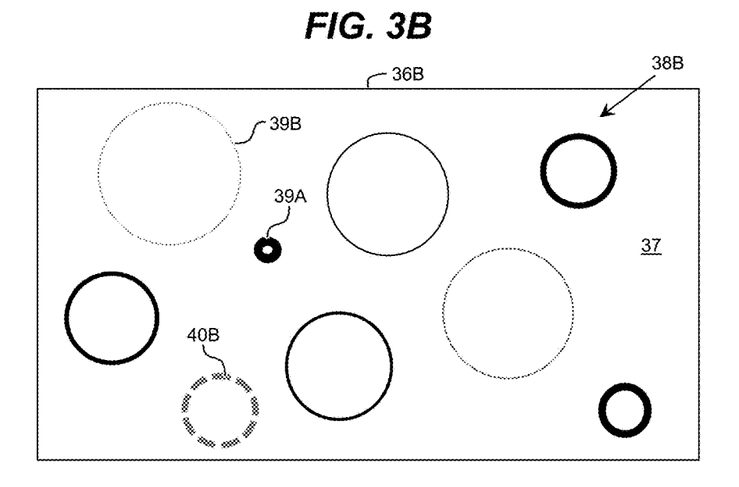

For example, FIGS. 3A and 3B show the targeting interfaces 36A, 36B including illustrative foreground blobs 40A, 40B, respectively, according to an embodiment. The computer system 20 can configure the foreground blobs 40A, 40B based on the corresponding background 38A, 38B and the visual function(s) being targeted. For example, each foreground blob 40A, 40B can have a subset of identical attributes which are selected to match the corresponding attribute(s) of the background 38A, 38B and a subset of targeting attributes selected to differ from the corresponding attribute(s) of the background 38A, 38B. The subset of targeting attributes can be selected based on the visual function(s) being targeted using any solution. While each targeting interface 36A, 36B is shown including a single foreground blob 40A, 40B, it is understood that a targeting interface 36A, 36B can concurrently include any number of zero or more foreground blobs 40A, 40B, which can appear concurrently or at staggered (e.g., random) intervals.

In an embodiment, the computer system 20 can generate one or more foreground blobs 40A, 40B with attributes that are selected such that all patients 14 should be able to detect the presence of the foreground blob 40A, 40B. Such foreground blobs 40A, 40B can be utilized to ensure that the targeting interface 36A, 36B is being properly presented to the patient 14 and that the patient 14 is properly prepared to view the targeting interface 36A, 36B and provide feedback. Concurrent with such foreground blob(s) and/or interchanged with the inclusion of such foreground blob(s), the computer system 20 can generate one or more foreground blobs 40A, 40B having attributes that are selected such that detection or non-detection of the foreground blob 40A, 40B is indicative of a condition of a targeted visual function. In an embodiment, the computer system 20 can generate multiple foreground blobs 40A, 40B (concurrently or over time) configured to target a visual function, but each of which varies from another by one or more attributes (e.g., contrast). The multiple foreground blobs 40A, 40B can present differing levels of difficulty for the patient 14 to detect each of the blobs 40A, 40B and/or distinguish each of the blobs 40A, 40B from the corresponding background 38A, 38B. In this case, the computer system 20 can use data regarding the number of and/or which blobs 40A, 40B that were detected by the patient 14 to evaluate a performance level for the targeted visual function.

Furthermore, for the targeting interface 36A, the foreground blob 40A can have any shape and/or size, including an amorphous or geometric shape, a changing shape, a changing size, and/or the like. For the targeting interface 36B, the foreground blob 40B can have a shape and changing size that is similar to the background FIGS. 39A, 39B of the background 38B, which also can be amorphous or defined. During the animation, the foreground blobs 40A, 40B can fade in and fade out from the targeting interface 36A, 36B. The foreground blobs 40A, 40B can remain in the corresponding background 38A, 38B for any duration of the animation. In an illustrative embodiment, the foreground blobs 40A, 40B remain present in the background 38A, 38B for only a portion of the animation, e.g., a period in a range of approximately 0.1 seconds to approximately ten seconds. In a more particular illustrative embodiment, the foreground blobs 40A, 40B can have fade in and fade out times, each of which is in a range of zero to approximately three seconds and a display interval of approximately 0.1 seconds to approximately ten seconds.

As used herein, a figure (e.g., a background FIG. 39A, 39B or a foreground area described herein) or a background 38A, 38B is substantially continuously changing when one or more attribute(s) change from frame to frame in the animation (e.g., video) or change in groups of frames such that the figure or background will not be perceived as having fixed attributes for any significant period of time (e.g., a half of second) by a patient 14 capable of perceiving the changes. It is understood that the term "animation," as used herein, is not limited to any particular type of technology for creating an appearance of motion (e.g., the changing background or figures described herein). To this extent, the term animation includes any solution for storing and/or generating a series of images or image-like depictions for presentation to an observer. In an embodiment, the animation comprises a video. As used herein, the term "video" encompasses all storage and presentation formats now known or later developed, which are capable of storing and presenting the substantially continuously changing background and/or figures described herein in a manner as described herein to an observer. Illustrative animation storage/generation solutions include: adjusting a display device using image data stored on a computer-readable medium; projecting a series of images (e.g., included in a film strip) onto a viewing surface; altering the on/off status of a series of lights arranged in a two-dimensional pattern; and/or the like.

In an illustrative implementation, the targeting interface 36A, 36B can be configured to occupy substantially an entirety of a display screen being viewed by the patient 14, e.g., to reduce other visual stimuli that may be presented on the display screen. Furthermore, the computer system 20 can store a set of data files, e.g., as assessment data 34, each of which includes an encoding of one or more video segments (e.g., scenes). The video data can be encoded using any solution, e.g., windows media video (WMV), Apple QuickTime Movie (MOV), and/or the like. In an embodiment, the computer system 20 repeatedly presents a video segment to the patient 14 until an indication corresponding to an ability of the patient 14 to perceive one or more foreground areas present in the video segment is received, a time period has expired, and/or the like.

In an embodiment, the computer system 20 can dynamically generate some or all of the animation, e.g., the background 38A, 38B, the foreground blob(s) 40A, 40B, and/or the like. In an embodiment, such dynamic generation is implemented using a randomized solution. For example, the computer system 20 can use a solution for generating random numbers, which the computer system 20 uses to dynamically determine one or more attributes of the image data, such that the animation does not repeat. To this extent, the computer system 20 can randomly and/or dynamically determine, for example: a color of one or more pixels in the background 38A; a location of one or more figures in the background 38B; one or more attributes of the changes (e.g., rate of change in size for a figure, a number/percent of pixels of a background changed each frame, and/or the like); and/or the like.

In the targeting interface 36A, the foreground blob 40A can have the same randomization as the background 38A, while one or more attributes, such as the colors, contrast, and/or the like, are varied in relation to the background 38A. In an embodiment, the varied attribute(s) (e.g., colors and contrast) of the foreground blob 40A appear similar in grayscale as the corresponding attributes of the background 38A. In the targeting interface 36B, the foreground blob 40B is also a substantially continuously changing figure, but can have one or more differing attributes (e.g., color and/or contrast) from that used with the background FIGS. 39A, 39B of the background 38B.

In an embodiment, the environment 10 (e.g., targeting interface 36A, 36B) can include a mechanism for concurrently presenting separate visual information to each eye of a patient 14 using the animation. For example, the targeting interface 36A, 36B may use polarization and/or anaglyph strategies to separately present visual information uniquely to each eye of a patient 14. In this case, when viewed binocularly, the contrasting foreground blob(s) 40A, 40B may be presented to one eye only, or, noise combined from the two eyes will produce an area of apparent elevation or depression from the plane of the background 38A, 38B or another characteristic that is not apparent when viewed with either eye singularly or when both eyes are used but the two images are not fully integrated in the visual cortex or "fused".

In an embodiment, the computer system 20 can determine the attributes for one or more of the foreground blobs 40A, 40B and/or the background FIGS. 39A, 39B of the background 38B in the targeting interfaces 36A, 36B based on the target visual function(s), a target performance level for each of the target visual function(s), and/or display attributes of a display environment in which the patient 14 will view the targeting interface 36A, 36B. Illustrative visual functions which can be targeted include: color detection (e.g., color deficiencies, color blindness, and/or the like), color sensitivity, contrast sensitivity, static visual acuity, dynamic visual acuity, refraction, binocular or eye muscle dysfunction, distance detection or depth perception, visual field or macular dysfunction, visual size differentiation, motion detection, and/or the like.

The computer system 20 can obtain the display attributes of the display environment using any solution. For example, the computer system 20 can use a default set of display attributes of a typical or known display environment. Illustrative display attributes can include one or more of: a distance from a display screen, a viewing angle of the patient 14 to the display screen, ambient lighting in the display environment, a size of the display screen, a resolution of the display screen, and/or the like. Furthermore, the computer system 20 can enable the user 12 and/or the patient 14 to alter one or more of the display attributes using any solution. For example, the computer system 20 can generate a user interface, which when presented to the user 12 and/or the patient 14, enables selection and alteration of one or more of the display attributes. In an embodiment, the computer system 20 can receive video input data of the patient 14 at the location at which the targeting interface 36 will be viewed from a camera having a known orientation with respect to the display screen. The computer system 20 can determine one or more of the display attributes by processing the video input data using any solution.

Once the target visual function(s), a target performance level for each of the target visual function(s), and/or display attributes of the display environment are available, the computer system 20 can determine the attributes of the background 38A, 38B and corresponding foreground blobs 40A, 40B to be displayed to the patient 14 using any solution. For example, depending on the target visual function(s), the computer system 20 can adjust one or more of: a color of a feature in the foreground blobs 40A, 40B and/or the background 38A, 38B; a contrast between two or more features in the foreground blobs 40A, 40B and/or the background 38A, 38B and/or between the foreground blobs 40A, 40B and the corresponding background 38A, 38B; a size and/or location of the foreground blobs 40A, 40B in the targeting interface 36A, 36B; a relative size between features in the foreground blob 40B; and/or the like. The computer system 20 can calculate the appropriate attributes using any solution. For example, to evaluate visual acuity of a patient 14, the computer system 20 can calculate attributes such that a size of a feature perceived by the patient 14 corresponds to a size utilized for a corresponding visual acuity used in a Snellen chart or other mechanism for evaluating visual acuity. In an embodiment, the computer system 20 can derive one or more of the shape attributes empirically, e.g., by repeatedly generating and observing perceptions using patients 14 with known performance level(s) for the target visual function(s).

While not shown, it is understood that the background 38A, 38B can include one or more additional features. For example, when the targeting interface 36A, 36B is used to target visual function(s) of a particular area of the visual field of a patient 14 (e.g., for assessment), the background 38A, 38B can include a focal point (e.g., a red dot, a cross, and/or the like), which remains in a constant location or moves, which the patient 14 is requested to focus. For example, the focal point can be located in a central portion of the background 38A, 38B and can remain fixed for a duration of the animation. As another example, the background 38A, 38B may be displayed using a polarization technique so that unique portions of the noise pattern are displayed to each eye individually that are not seen by the follow eye. This would allow the subject to view the background 38A, 38B with both eyes, binocularly, but while presenting unique features to each eye singularly.

As described herein, the computer system 20 can use a targeting interface 36A, 36B to assess a performance level of the patient 14 with respect to one or more visual functions. To this extent, the computer system 20 can generate an animation including a background 38A, 38B and one or more foreground blobs 40A, 40B described herein for inclusion in the targeting interface 36A, 36B and presentation to the patient 14 using any solution. It is understood that at various times during the animation, any number of zero or more foreground blobs 40A, 40B may be present in the targeting interface 36A, 36B.

Furthermore, the computer system 20 can receive an indication corresponding to an ability of the patient 14 to distinguish the foreground blob(s) 40A, 40B from the background 38A, 38B in the animation using any solution. For example, the targeting interface 36A, 36B can include an ability for the patient 14 and/or user 12 to enter the information using a user interface control (e.g., a button, a touchscreen, or the like), which is subsequently received by the computer system 20. Similarly, the computer system 20 can receive and process an indication spoken by the patient 14 and/or the user 12. In an embodiment, when a location of the foreground blob 40A, 40B is moving within the background 38A, 38B, the indication includes a perceived direction of movement (e.g., right/left, up/down, clockwise/counterclockwise, and/or the like) of the foreground blob 40A, 40B, which the computer system 20 can compare with the actual simulated movement for accuracy. Still further, the computer system 20 can receive video data including the eyes of the patient 14, and process the video data to determine when the patient 14 directs his/her direction of gaze to the foreground blob(s) 40A, 40B in the targeting interface 36A, 36B and correlate the patient's 14 direction of gaze with his/her ability to distinguish the foreground blob(s) 40A, 40B from the background 38A, 38B.

Embodiments of the invention can be directed to solve an existing technical problem with assessing visual function(s) of a patient 14. For example, the traditional use of static letters or pictograms in assessing a visual function relies on an evaluation of a statistically meaningful number of errors, misidentifications, or confusions of the naming of static letters or pictograms made by the patient 14. In contrast, an embodiment of the invention uses a background and foreground blob(s), each with one or more randomized, dynamic, contrasting features to assess the visual function(s). In this case, the identification task is distinctly different in that it relies only on awareness of the distinct appearance of a foreground blob or not rather than the additional cognitive overhead involved in the non-visual cortex with processing and naming letters, pictograms, and shapes. Furthermore, an embodiment of the invention can identify a perceptual threshold of the visual function(s) of a patient 14 using a binary "on or off" indication. Embodiments of the invention can be applied to assessing any of various visual functions (e.g., static visual acuity, dynamic visual acuity, refraction, binocular or eye muscle dysfunction, distance detection, visual size differentiation, motion detection, color detection (e.g., color deficiencies, color blindness, and/or the like), color sensitivity, contrast sensitivity, and/or the like) or visual fields.

In a more particular illustrative embodiment, the computer system 20 can generate an animation including one of the targeting interfaces 36A, 36B for presentation to the patient 14. During the animation, the computer system can generate and superimpose foreground blob(s) 40A, 40B onto the corresponding background 38A, 38B, respectively. Additionally, the computer system 20 can receive feedback from the patient 14 as to whether he/she sees the foreground blob(s) 40A, 40B, and if so, when and where the foreground blob(s) 40A, 40B were first identified. The computer system 20 can use the feedback data regarding the (in)visibility and/or (in)distinguishability of the foreground blob(s) 40A, 40B to assess: color deficiencies, color blindness or sensitivity to color, contrast sensitivity, dynamic or static visual acuity, visual field or macular dysfunctions, eye muscle dysfunction, and/or the like.

In another more particular illustrative embodiment, the computer system can target visual function(s) without the use of foreground blob(s) 40A, 40B. For example, during the animation, the computer system 20 can vary one or more attributes of the background 38A, 38B over time and receive feedback as to whether such variation is perceived by the patient 14. Furthermore, in an embodiment, the computer system 20 can receive feedback from the patient 14 as to areas within the randomized background 38A, 38B that appear either missing or noticeably changed in appearance compared to the generally uniform randomized background 38A, 38B, which indicate a localized change in the random pattern. The computer system 20 can use the feedback data to define localized changes in retinal function of the patient 14. Additionally, selection of specific colors comprising the randomized background 38A, 38B can be used to further define types of retinal cell populations of the patient 14 that are affected. The patient 14 can provide the feedback to the computer system 20 verbally, by manual selection of an area, by pointing to the specific areas of the targeting interface 36A, 36B where the localized changes are apparent, and/or the like.

In an illustrative example, the computer system 20 can use the feedback to assess whether the patient 14 has a problem with his/her macula. In this case, the patient 14 may report seeing a hole in a central region of his/her vision (e.g., a lack of any noise or pattern in the area), and/or the like. In another illustrative example, the computer system 20 can generate an animation configured to target differing colors in different regions of the vision of the patient 14. For example, the animation can include a higher density of color pixels in a central region to target the corresponding higher density of color sensors present in the central portion of the retina of the patient 14, while the outer regions of the background 38A, 38B include more black and white pixels.

Aspects of the invention described herein can be used in other applications apart from assessing visual function(s) of a patient in a medical treatment context. For example, the appearance/disappearance of a foreground blob 40A, 40B may be used with a polarized targeting display to treat binocularity disorders resulting in one eye being suppressed with poor corrected visual acuity.

While primarily shown and described herein as a method and system for assessing visual function(s) of a patient, it is understood that aspects of the invention further provide various alternative embodiments. For example, in one embodiment, the invention provides a computer program fixed in at least one computer-readable medium, which when executed, enables a computer system to assess visual function(s) of a patient using a process described herein. To this extent, the computer-readable medium includes program code, such as the assessment program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the assessment program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for assessing visual function(s) of a patient. In this case, the generating can include configuring a computer system, such as the computer system 20 (FIG. 1), to implement a method of assessing visual function(s) of a patient described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A method of targeting a visual function of an observer, the method including:
    presenting a series of images to the observer, each image in the series of images including a background, wherein at least a portion of the series of images further includes a foreground area in a portion of the background, wherein the background and the foreground area include a set of common attributes that change in each image of the series of images and at least one different attribute between the background and the foreground area, wherein the set of common attributes that change in each image of the series of images result in a changing appearance of the background and the foreground area in the series of images, wherein the at least one different attribute targets the visual function, and wherein at least one attribute of the background changes randomly in each image of the series of images; and
    receiving an indication corresponding to an ability of the observer to perceive the foreground area in response to observing at least some of the series of images, without requiring the observer to identify any of: a letter, a number, or a pictogram.

2. The method of claim 1, wherein each of the background and the foreground area is a random arrangement of pixels of at least two colors, wherein the random arrangement of pixels changes for each image of the series of images.

3. The method of claim 1, wherein each of the background and the foreground area includes a set of figures, and wherein each figure changes in appearance for each image of the series of images in which the figure is included.

4. The method of claim 3, wherein the set of figures for each of the background and the foreground area is a set of ellipses, wherein each ellipse is visible in only a portion of the series of images, and wherein each ellipse has an increasing size and a decreasing brightness during the portion of the series of images.

5. The method of claim 3, wherein each figure includes a transparent center.

6. The method of claim 1, wherein the generating includes dynamically creating at least a portion of the series of images using a randomized solution.

7. The method of claim 1, wherein the presenting includes concurrently presenting separate visual information to each eye of a patient using the series of images.

8. The method of claim 1, wherein the series of images are presented to the observer as an animation with a substantially continuously changing appearance of the background and the foreground area.

9. The method of claim 8, wherein the receiving an indication includes evaluating objective electronic input data of the observer to correlate the ability of the observer to perceive the foreground area.

10. The method of claim 1, wherein the targeting is performed as part of a visual assessment process.

11. The method of claim 1, wherein at least one of: a location or a size, of the foreground area changes in the series of images.

12. The method of claim 1, wherein the foreground area appears to be moving in the series of images.

13. The method of claim 1, wherein a size of at least one feature in the foreground area changes in the series of images.

14. A method of assessing a visual function of an observer, the method including:
    presenting a series of images to the observer, each image in the series of images including a background, wherein at least a portion of the series of images further includes a foreground area in a portion of the background, wherein the background and the foreground area include a set of common attributes that change in each image of the series of images and at least one different attribute between the background and the foreground area, wherein the at least one different attribute targets the visual function, wherein the set of common attributes that change in each image of the series of images result in a changing appearance of the background and the foreground area in the series of images, and wherein at least one attribute of the background changes randomly in each image of the series of images;
    receiving an indication corresponding to an ability of the observer to perceive the foreground area in response to presenting at least some of the series of images, without requiring the observer to identify any of: a letter, a number, or a pictogram; and
    providing the indication for use in assessing the target visual function of the observer.

15. The method of claim 14, wherein each of the background and the foreground area is a random arrangement of pixels of at least two colors, wherein the random arrangement of pixels changes for each image of the series of images.

16. The method of claim 14, wherein each of the background and the foreground area includes a set of figures, wherein each figure changes in appearance for each image of the series of images in which the figure is included.

17. The method of claim 16, wherein the set of figures are a set of ellipses, wherein each ellipse is visible in only a portion of the series of images, and wherein each ellipse has an increasing size and a decreasing brightness during the portion of the series of images.

18. The method of claim 14, wherein the target visual function is one of: static visual acuity, dynamic visual acuity, refraction, binocular muscle dysfunction, eye muscle dysfunction, distance detection, visual size differentiation, motion detection, color detection, color sensitivity, or contrast sensitivity.

19. A method of assessing a visual function of an observer, the method including:
    presenting a series of images to the observer, each image in the series of images including a background, wherein at least a portion of the series of images further includes a foreground area in a portion of the background, wherein the background and the foreground area include a set of common attributes that change in each image of the series of images and at least one different attribute between the background and the foreground area, wherein the at least one different attribute targets the visual function, wherein the set of common attributes that change in each image of the series of images result in a changing appearance of the background and the foreground area in the series of images, and wherein at least one attribute of the background changes randomly during the series of images;
    receiving an indication corresponding to an ability of the observer to perceive the foreground area in response to observing at least some of the series of images, without requiring the observer to identify any of: a letter, a number, or a pictogram; and
    providing the indication for use in assessing the target visual function of the observer.

20. The method of claim 19, wherein each of the background and the foreground area is a random arrangement of pixels of at least two colors, wherein the random arrangement of pixels changes for each image of the series of images.

21. The method of claim 19, wherein each of the background and the foreground area includes a set of figures, and wherein each figure changes in appearance for each image of the series of images in which the figure is included.

22. The method of claim 21, wherein the set of figures are a set of ellipses, wherein each ellipse is visible in only a portion of the series of images, and wherein each ellipse has an increasing size and a decreasing brightness during the portion of the series of images.

23. The method of claim 19, wherein the assessing includes repeating the receiving and providing for a plurality of foreground areas included in the series of images.

24. The method of claim 19, further comprising dynamically creating at least a portion of the series of images using a randomized solution.

25. The method of claim 19, wherein the target visual function is one of: static visual acuity, dynamic visual acuity, refraction, binocular muscle dysfunction, eye muscle dysfunction, distance detection, visual size differentiation, motion detection, color detection, color sensitivity, or contrast sensitivity.

* * * * *